(12) United States Patent
Tranchant et al.

(10) Patent No.: US 6,280,713 B1
(45) Date of Patent: *Aug. 28, 2001

(54) NAIL VARNISH CONTAINING MICROGELS

(75) Inventors: Jean-François Tranchant, Boigny sur Bionne; Henri-Gérard Riess, Mulhouse; Alain Meybeck, Courbevoie, all of (FR)

(73) Assignee: LVMH Recherche (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,385

(22) PCT Filed: Sep. 28, 1995

(86) PCT No.: PCT/FR95/01252

§ 371 Date: Mar. 28, 1997

§ 102(e) Date: Mar. 28, 1997

(87) PCT Pub. No.: WO96/10044

PCT Pub. Date: Apr. 4, 1996

(30) Foreign Application Priority Data

Sep. 28, 1994 (FR) ................................................. 94 11575
Sep. 28, 1994 (FR) ................................................. 94 11576
Apr. 6, 1995 (FR) ................................................. 95 04120

(51) Int. Cl.$^7$ ............................. A61K 7/04; A61K 7/00; C08F 118/02; C08F 136/08

(52) U.S. Cl. ............................. 424/61; 424/401; 526/319; 526/320; 526/321; 526/327; 526/329; 526/340.2; 526/346

(58) Field of Search .................. 424/61, 401; 526/317.1, 526/319, 320, 321, 327, 329, 340.2, 346; 525/184

(56) References Cited

U.S. PATENT DOCUMENTS

| | | |
|---|---|---|
| 4,414,357 | 11/1983 | Wright et al. |
| 4,747,419 * | 5/1988 | Flynn ..................................... 132/73 |
| 5,298,585 * | 3/1994 | McCallum ........................ 526/317.1 |
| 5,338,815 * | 8/1994 | Aizawa ................................ 526/306 |
| 5,711,940 * | 1/1998 | Kuentz et al. ......................... 424/61 |
| 5,916,985 * | 1/1999 | Tondeur et al. ...................... 526/214 |
| 5,985,998 * | 11/1999 | Sommerfield et al. ................. 525/72 |

FOREIGN PATENT DOCUMENTS

| | | |
|---|---|---|
| 207026 | 12/1986 | (EP) . |
| 254467 | 1/1988 | (EP) . |
| 267726 | 5/1988 | (EP) . |
| 408189 | 1/1991 | (EP) . |

OTHER PUBLICATIONS

S. Ishikura "Zwitter ion modified epoxy resins that serve as emulsifier in the microgel forming emulsion polymerization reaction" ACS Org. Coatings and Polym. Sci.Pro.48,989 (1983).

W. Funke et al. "Intramolecularly crosslinked Macromolecules—Formation and Structure, Characterization and Particle Properties" Polymer International, 30, 519 (1993).

D. Kuhnle et al. "Uber die Reaktionsfahigkeit der Vinylgruppen in vernetzten Diviny lbenzol–Polymeren und Styrol/Divinylbenzol–Copolymeren", Makromol, Chem. 139, 255 (1971).

W. Beer et al. "Darstellung raumlich vernetzten Polymere aus difunktionellen Monomeren und reaktiven polyfunktionellen Microgel–und Gelpartikeln", Angew. Makromol, Chem.23, 205 (1972) No translation.

W. Obrecht et al. "Zur Herstellung von reaktiven Microgelen durch Emulsion Polymerisation von reinen mehrfunktionellen Vinylmonomeren" Makromol. Chem., 175, 3587 (1974).

S. Ishikura et al. "Flow and film properties of coatings containing microgels", Prog. in Org. Coat., 15, 373 (1988).

H. Muramoto et al. "Design of microgel–containing Coatings", Proceedings 13th Int. Conf. Org. Coat. Sci. Techn., 237 (1987).

W. Funke et al. "Emulsion Polymerization of Unsaturated Polyester Resins", Makromol, Chem., 180, 2797 (1979).

Ch. Yu et al. "Reactive microgels by emulsion polymerisation of unsaturated polyester resins", Makromol, Chem., 103, 187 (1982).

H. Baumann et al. "Emulsifying properties of saturated polyesters", Makromol, Chem., 187, 2933 (1986).

E.J. Goethals, "Telechelic Polymers Synthesis and Applications", CRC Press Inc. (1989), pp. 169–179.

* cited by examiner

*Primary Examiner*—Russell Travers
*Assistant Examiner*—Shengjun Wang
(74) *Attorney, Agent, or Firm*—Bierman, Muserlian and Lucas

(57) ABSTRACT

The invention relates to novel microgel-containing essentially organic solvent nail varnishes.

The microgels are particularly acrylic microgels.

The invention also relates to the use of these microgels for modifying the physical properties of an essentially organic solvent nail varnish composition, and/or the properties of the film obtained during the application of said composition.

44 Claims, No Drawings

NAIL VARNISH CONTAINING MICROGELS

This application a 371 of PCT/FR95/01252, filed Sep. 28, 1995, which claims the priority of French application 94/11575, filed Sep. 28, 1994, 94/11576, filed Sep. 28, 1994, and 95/04120, filed Apr. 6, 1995.

The invention related to novel nail varnishes containing microgels as well as to the use of these microgels for modifying the physical properties of said vanishes and/or film obtained.

The present invention is situated most particularly in the field of nail varnishes comprising an essentially non-aqueous organic solvent medium. In such nail varnishes, the solvent or the mixture of solvents conventionally represents between 50 and 80% by weight of the total weight of the nail varnish. The organic solvents which are conventionally used are low molecular weight esters, particularly ethyl, propyl or butyl acetates. The organic solvent medium may also contain low molecular with alcohols, particularly ethanol, isopropanol or butanol, or ketones, particularly acetone or methyl or methyl ketone.

In the sense of the invention, <nail varnish comprising an essentially non-aqueous organic solvent> or more simply <organic solvent nail varnish> will refer to nail varnishes in which the solvent comprises at most 1% water and is composed of at least one of the solvents defined above.

Generally, organophilic clays are used in the organic solvent nail varnishes for preventing the sedimentation of pigments. Smectites, hectorites, bentonites and quaternised montmorillonites will be cited as examples of organophilic clays commonly used to this end. The use of these products has disadvantages which are well-known to nail varnish formulators: in fact, they strongly lower the adhesion of the varnish, furthermore they also lower its brightness and, the other disadvantage is that they generally necessitate the presence of toluene in the formulation.

Generally, in nail varnishes comprising an organic solvent, the main part of the dry extract is due to the presence of nitrocellulose.

The applicant has now discovered that a part or even the whole of the nitrocellulose contained in the organic solvent nail varnishes could be replaced by microgels and that furthermore, in a totally surprising way, the presence of microgels in the nail varnish compositions enabled improving the rheological properties of the varnish and/or film, particularly enabling preventing the precipitation of the pigments. This remarkable property enables appreciably lowering, even doing away with the amount of organophilic clays generally used to this end in nail varnishes, but whose disadvantages are well-known, as it has been revealed above.

Furthermore, nail varnish formulation specialists know that, amongst the other problems to be solved, it is notably essential to find a good compromise which enables having a high dry extract without however increasing the viscosity of the product in too significant a way. This is particularly sharp when the preparation of a varnish enabling obtaining a beautiful aspect of the nail surface with one sole varnish layer is sought-after. Such a varnish is commonly referred to as <one coat> by the person skilled in the art.

In fact, in order for a varnish of this type may, in one sole layer, form a film that covers sufficiently, it is generally necessary to increase the amount of pigments. However, it is necessary to watch so as not to exceed a certain pigment concentration, since it would be possible for this to be detrimental to the brightness of the film obtained. It could be possible to consider increasing the thickness of the film by increasing the quantity of nitrocellulose and/or resin, but in this case, a problem of application of the varnish is come up against due to too high a viscosity. In order to attempt to solve this problem, it has been proposed to lower the grade of the nitrocellulose used, but then the quality of the film is decreased and it becomes more fragile and chips.

Now, the applicant has demonstrated that the incorporation of a microgel in a nail varnish formula enabled increasing the dry extract of the varnish in a surprising way without meaning appreciably increasing its viscosity.

Thus, the present invention enables in particular providing a solution to the problem of the formulation of <one coat> nail varnishes such as defined above.

According to one of its essential characteristics, the invention relates to nail varnishes comprising an essentially non-aqueous organic solvent medium containing, as well as the usual constituents of nail varnishes, at least one microgel, said microgel not being obtained from an acrylic polymer microdispersion prepared by radical polymerisation of at least one acrylic monomer in the presence of a poly(methyl methacrylate) (PMMA). (PMMA) or a poly(tert-butyl acrylate) (PtBuA)-based block copolymer.

The microgel which can be used for preparing the nail varnishes according to the invention may be any microgel, in particular the microgels such as have been defined by W. FUNKE et al., <Intramolecularly Crosslinked Macromolecules. Formation and structure. Characterization and Particules Properties>, Polym. Internat., 30, 519, (1993). In this publication, FUNKE et al. give a complete definition of the microgels in insisting on the following points: the solubility being a characteristic common to microgels and linear polymers, the microgels differ from the linear or branched polymers by a three-dimensional cross-linked network. The diameters of their particles is lower than 100 nm and their molecular mass is in general greater than $10^6$ g/mol. From this fact, it is possible for the microgels to be dispersed in order to form transparent or slightly opalescent colloidal solutions.

The microgels obtained from an acrylic polymer microdispersion prepared by radical polymerisation of at least one acrylic monomer in the presence of a poly(methyl methacrylate) (PMMA)- and tert-butyl polyacrylate (PAtBu)-based block copolymer have intentionally been excluded from the list of usable microgels according to the invention in order to take into account U.S. Pat. No. 5,711,940 which provides stable microdispersions and microgels based on acrylic polymers, as well as the method of obtaining them, and compositions, notably cosmetic compositions composing them.

According to a particularly advantageous variant of the invention, the microgel comprises a cross-linked polymer based on a monofunctional monomer known as principal monomer, and a difunctional monomer acting as cross-linking agent.

The principal monomer will advantageously be selected from the acrylic, methacrylic, styrenic or vinylic ester monomers. Preferably said vinyl ester has a C1 to C18 alkyl group.

More specifically, these monomers will be selected from the family comprising:
 the alkylacrylates and alkylmethacrylates having linear or branched C1 to C6 alkyl groups, or a mixture thereof,
 styrenic monomers,
 vinylic esters having C1 to C8 alkyl groups, for example vinyl acetate.

The difunctional monomers of cross-linking agent function will advantageously be selected from the following, for example butandiol dimethacrylate, diethyleneglycol dimethacrylate, diethyleneglycol dimethacrylate, tetraethyleneglycol dimethacrylate, the difunctional aromatic monomers, for example divinylbezene.

The various monomers in the family of monomers of the acrylic or methacrylic type will be preferentially selected. The proportion of cross-linking of the microgels represented by the proportion of difunctional monomer with respect to the monofunctional monomer is advantageously between 0.5 and 40% by weight, preferably between 0.5 and 15%.

Such microgels are, for certain ones, commercially available. The microgels marketed by Nippon Paint will particularly be cited.

It is also possible for these microgels to be obtained by swelling a microlatex prepared by radical polymerisation of a monofunctional monomer such as defined above, in a solvent and in the presence of a cross-linking monomer and a surfactant, preferably an anionic surfactant.

In order to prepare these microgels, micellar solutions of surfactants will be particularly prepared in the presence of which the microlatexes will be prepared by any polymerisation method in the presence of an organosoluble or hydrosoluble initiator as described by W. Funke with saturated or unsaturated polyesters, in particular in:

"Emulsifying properties of saturated polyesters" H. BAUMANN, B. JOOS, W. FUNKE, Makromol. Chem., 187, 2933 (1986), "Saturated polyesters as emulsifiers for emulsion copolymerization of unasaturated polyester resins with styrene" H. BAUMANN, B. JOOS, W. FUNKE Makromol. Chem., 190, 83–92 (1989), "Reactor Microgels by Self-emulsifying Copolymerization of Unsaturated Polyester Resins with Acrylic and Methacrylic Esters" Makromol. Chem., 184, 755–762 (1983) M. MIYATA, W. FUNKE "Reactive Microgels by Emulsion Polymerization of Unsaturated Polyester Resins" Y.-Ch. YU, W. FUNKE Die Angewandte Makromol. Chem., 103, 187–202 (1982), "Surfactant Properties of Unsaturated Polyesters" Y.-Ch. Yu, W. FUNKE Die Angewandte Makromol. Chem., 103, 203–215 (1982).

In order to prepare the microlatexes that are then converted into microgels before their incorporation in the varnishes according to the invention, various surfactants cited in the literature may be used, in particular conventional anionic surfactants, particularly sodium dodecylsulphate whose bibliographic references art the following:

D. KÜHNLE et W. FUNKE, "Über die Reaktionsf ähigkeit der Vinylgruppen in vernetzten Divinylbenzol-Polymeren und Styrol-Divinylbenzol-Copolymeren", Makromol. Chem., 139, 255, (1971)

W. BEER, D. KÜHNLE et W. FUNKE, "Darstellung ra ümlich vernetzten Polymere aus difunktionellen Monomeren und reaktiven polyfunktionellen Microgel-und Gelpartikeln", Angew: Makromol. Chem., 23, 205 (1972)

W. OBRECHT, U. SEITZ et W. FUNKE, "Zur Herstellung von reaktiven Microgelen durch Emulsion Polymerisation von reinen mehrfunktionellen Vinylmonomeren", Makromol. Chem., 175, 3587 (1974);

conventional cationic surfactants as describes in S. ISHIKURA, K. ISHII and R. MIZUGUSHI, "Flow and film properties of coatings containing microgels", Prog. in Org. Coat., 15, 373 (1988), non-ionic surfactants, particularly polyoxyethylene-polyoxy-propylene (POE-POP), as described in EP O 267 726, mixtures of conventional surfactants and non-ionic surfactants as described in German patent DE-3 723 274, epoxy resins modified by zwitterions, as described in H. MURAMOTO, K. ISHII, T. MUYAZONO, S. ISHIKURA and R. MIDZUGUSHI, "Design of microgel-containing Coatings", Proceedings 13th Int. Conf. Org. Coat. Sci. Techn., 237 (1987) and in S. ISHIKURA, "Zwitter ion Modified Epoxy Resins that serve as Emulsifier in the Microgel Forming Emulsion Polymerization Reaction", ACS Org. Coatings and Polym. Sci Proc., 48, 989 (1983), saturated and unsaturated polyesters as described in W. FUNKE, R. KOLITZ and W. SRAEHLE, "Emulsion Polymerization of unsaturated polyester resins", Makromol, Chem., 180, 2797 (1979), in Y. Ch. YU et W. FUNKE, "Reactive microgels by emulsion polymerisation of unsaturated polyester resins", Angew. Makromol. Chem., 103, 187 (1982) and in H. BAUMANN, B. JOOS and W. FUNKE, "Emulsifying properties of saturated polyesters", Makromol. Chem., 187, 2933 (1986), sulphosuccinates as described in U.S. Pat. No. 4,414, 357.

Macromolecular surfactants, in particular polyesters functionalised with carboxyl groups will be advantageously selected.

According to another particularly advantageous variant of the invention, the macromolecular surfactant will belong to a first family (I) constituted:

of functionalised polymers of the formula:

$$(P)\text{-}S\text{-}X\text{-}F \tag{1}$$

in which:

(P) is a hydrophobic polymer chain of number average molar mass between 500 and 250,000, S represents sulphur, X represents:

a saturated or unsaturated linear or branched hydrocarbon chain having 1 to 6 carbon atoms and substituted with at least one COOH or $NH_2$ group, in the free or salified form;

a peptide chain constituted of 2 to 4 amino acids, particularly natural amino acids;

F represents a COOH or $NH_2$ group, in the free or salified form, and polymers resulting from the radical polymerisation of at least one monomer in the presence of a peptide bearing at least one disulphide group and/or at least one thiol function, such as a keratin hydrolysate.

The polymer chain (P) is advantageously obtained by radical polymerisation of an acrylic or vinylic monomer.

Amongst the acrylic monomers, the acrylates, methacrylates and ethylacrylates of a saturated or unsaturated C1 to C18 hydrocarbon group, particularly a linear, branched or cycle-containing allylic group, will most particularly be cited.

A preferred monomer according to the invention for preparing the polymer chains (P) above is methyl methacrylate.

Amongst the vinylic monomers, styrene, alpha-methyl styrene, substituted styrenes, acrylonitrile, vinylic esters such as vinyl acetate will notably be cited.

Amongst the mixtures of monomers, mixtures of alkyl acrylate or methacrylate and allyl acrylate or methacrylate will be particularly cite, more particularly mixtures of methyl methacrylate and allyl methacrylate. The advantage of such monomer mixtures is that they lead to partially unsaturated polymer chains which enable obtaining specific properties of the polymers linked to the presence of these unsaturated bonds in the polymer chain.

Particular products of the family of polymers (I) above have been described by:

Y. YAMASHITA, Y. CHUJO, H. KOBAYASHI and KAWAKAMI in Polym. Bull., 5, 361–366 (1981); this publication describes macromonomers of general formula (PMMA) SCH(COOH)CH$_2$COOH as well as other acrylic macromonomers having the same terminal function. All these macromonomers are intended to be used in polycondensation operations;

Y. CHUJO, H. KOBAYASHI and Y. YAMASHITA in J. of Polym. Sci., Part A: Polym. Chem., 27, 2007–2014 (1989); this publication describes macromonomers also intended for polymerisation operations, these macromonomers being constituted of a PMMA polymeric chain terminated with a dicarboxylic aromatic functional group.

The various pieces of work by YAMASHITA, CHUJO et al. have provided certain polymers of this family obtained by radical polymerisation of a monomer in the presence of thiomalic acid. The products according to the invention, usable as macromolecular surfactant, can be obtained in a method analogous to that described in the above-mentioned pieces of work by YAMASHITA, CHUJO et al., but using various other chain transfer agents during the radical polymerisation. These chain transfer agents being constituted by thiols or disulphides which are capable of being decomposed in order to generate thiol groups acting in turn as chain transfer agent.

Thus, according to a variant, it will be possible for the functionalised polymer serving as macromolecular surfactant to result from the radical polymerisation of a monomer in the presence of a thiol of formula H-S-X-F or a disulphide of formula F-X-S-S-X-F in which: X represents:

a saturated or unsaturated linear or branched hydrocarbon chain having 1 to 6 carbon atoms and substituted with at least one COOH or NH$_2$ group, in the free or salified form, a peptide chain constituted of 2 to 4 amino acids, particularly natural amino acids, F represents a COOH or NH$_2$ group, in the free or salified form, said thiol or disulphide acting as chain transfer agent during said radical polymerisation, said monomer (s) leading to the formation of the polymer chain (P) such as defined above.

As it has been pointed out above, the principles of the synthetic method is directly inspired from the work of YAMASHITA, CHUJO et al. who have developed this type of macromonomers with the aim of copolymerising them by copolymerisation and thus forming graft copolymers (see particularly, E. J. GOETHALS, "Telechelic Polymers Synthesis and Applications" CRC Press, Inc, 169–179 (1989).

The principle of this synthesis consists of radical polymerising methyl methacrylate in the presence of a transfer agent bearing acid functions, in this case thiomalic acid, under the conditions indicated in the reaction scheme (I) below:

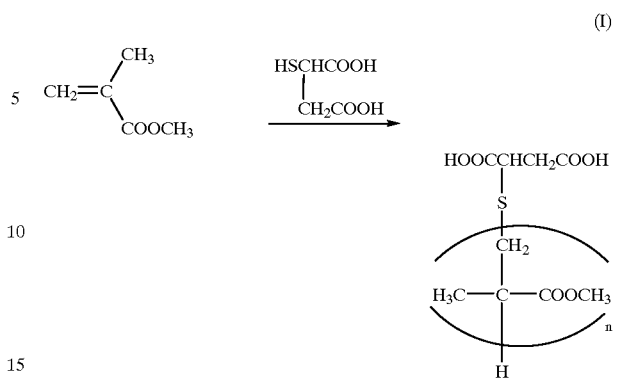

This reaction is carried out in a solvent medium, e.g. THF, in the presence of a radical polymerisation initiator, e.g. azobisisobutyronitrile (AIBN), at a temperature in the order of 60° C.

It will be possible for the functionalised polymers according to the invention to be advantageously prepared by an analogous method inspired from the reaction scheme (I) above by selecting them monomer(s) and the thiol according to the final product sought-after.

The radical polymerisation reaction of the monomer(s) will be carried out in a solvent medium in the presence of a radical polymerisation agent constituted of an organosoluble initiator preferably selected from the family of azo initiators.

Azobisisobutyronitrile (AIBN) will be cited as an example of a preferred initiator.

The reaction takes place in a solvent medium.

The solvent or the mixture of solvents will be selected according to the nature of the monomer(s) to be polymerised and the thiol.

The solvent or the mixture of solvents will be selected according to the nature of the reagents. Preferably, it will be matter of a solvent or a mixture of solvents which is capable of dissolving the whole of the reagents present, namely the monomers, the polymer forme, the initiator and the transfer agent.

The solvent may have an acidic character, acetic acid will be used for example; it may also have a basic character, e.g. dimethylethanolamine.

The reaction temperature will advantageously be between 30° C. and 120° C., but is to be adjusted according to the reagents present. It is easily understood that it depends on the nature of the initiator and the nature of the solvent.

The molecular mass of the functionalised polymer resulting from the process described above will be controlled in adjusting the amount of chain transfer agent introduced.

The proportions of initiator, transfer agent and monomer (s) may be calculated according to the classical relationship known for chain transfer:

$$\frac{1}{DPn} = \frac{1}{DPn_0} + Cs\left(\frac{S}{M}\right)$$

wherein

S/M is the thiol/monomer molar ratio to be applied,

Cs is the transfer constant depending on the nature of the monomer(s), the transfer agent, the temperature and the solvent, DPn is the degree of polymerisation of the polymer that is desired to be synthesised, $DPn_0$ is the degree of polymerisation of the polymer that would have been obtained in the absence of a transfer agent.

Generally, in order to prepare functionalised polymers of the formula (I) described above, a thiol of formula H—S—X—F, wherein X and F have the meanings given above, will be used as chain transfer agent.

According to a variant of the method, it will be possible for a disulphide of formula F—X—S—S—X—F to be used this disulphide is splitable into two F—X—S radicals under the conditions of the radical polymerisation, these two radicals acting in a way which is analogous to what happens in the presence of the corresponding thiol H—S—X—F.

The thiols which are useful which are useful for preparing the compounds according to the invention are all the compounds of formula H—S—X—F in which:

X represents:
- a saturated or unsaturated linear or branched hydrocarbon chain having 1 to 6 carbon atoms and substituted with at least one COOH or $NH_2$ group, in the free or salified form,
- a peptide chain constituted of 2 to 4 amino acids, particularly natural amino acids, F represents a COOH or $NH_2$ group, in the free or salified form, with the exception of thiomalic acid.

The disulphides which are useful for preparing the functionalised polymers of the family according to the invention are the disulphides of formula F—X—S—S—X—F wherein X and F have the meanings given above.

Particularly preferred functionalised polymers according to the invention are those in which the F—X part comprises at least one carboxylic function and at least one amine function, in the free or salified form.

As examples of such polymers those in which the chain transfer agent is cysteine or homocysteine will be cited.

The functionalised polymers which result from the radical polymerisation of at least one monomer in the presence of cysteine acting as chain transfer agent will most particularly be cited.

Such a functionalised polymer following that it is in the free or salified form is of one of the formulae:

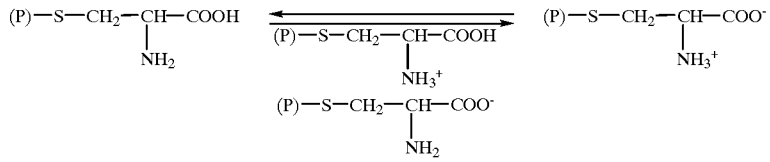

wherein (P) is a hydrophobic polymer chain resulting from the radical polymerisation of at least one monomer.

It will also be possible for the functionalise polymers of the family (I) to result form the radical polymerisation of a monomer in the presence of a thiol of formula H—S—X—F or a disulphide of formula F—X—S—S—X—F in which:

X represents:
- a saturated or unsaturated linear or branched hydrocarbon chain having 1 to 6 carbon atoms and substituted with at least one COOH or $NH_2$ group, in the free or salified form;
- a peptide chain constituted of 2 to 4 amino acids, particularly natural amino acids;

F represents a COOH or $NH_2$ group, in the free or salified form, said thiol or disulphide acting as chain transfer agent during said radical polymerisation, said monomer(s) leading to the formation of the polymer chain (P) such as defined above.

The polymer chains (P) defined above have preferably a number average mass lower than 20,000, even preferably between 500 and 10,000.

Amongst the products described above, those in which the F—X part comprises at least one carboxylic function and at least one amine function in the free or salified form will preferably be selected.

As examples of functionalised polymers of the family (I), the product of formula:

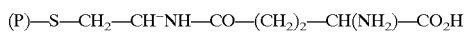

will be cited and more particularly the functionalised polymer obtained by radical polymerisation of a monomer leading to the polymerised chain such as defined above in the presence of a chain transfer agent constituted of glutathione.

According to other advantageous variants of the invention, the radical polymerisation will be carried out of the monomer leading to the formation of the polymer chain P defined above in the presence of cysteine or homocysteine which will act as chain transfer agent. It will also be possible for a peptide bearing at least one disulphide group and/or at least one thiol function to be used, such as a keratin hydrolysate.

According to another variant of the invention, it will be possible for the macromolecular surfactant to be a chain end-functionalised polymer of the formula

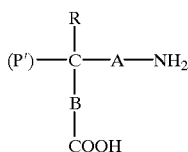

(II)

in which:
the polymer chain (P') is an advantageously hydrophobic chain obtained by radical polymerisation of at least one monomer, and whose number average molar mass is between 500 and 250,000, preferably lower than 20,000, preferably between 500 and 10,000, R represents a hydrogen atom or a linear or branched hydrocarbon chain having 1 to 8 carbon atoms optionally substituted with at least one group selected from $CO_2H$, $NH_2$, OH or a phenyl group, itself being optionally substituted, A and B, identical or different, each represent a single bond, a saturated or unsaturated linear or branched hydrocarbon chain having from 1 to 16 carbon atoms, it being possible for it to contain an amide bond or a peptide chain having 2 to 4 amino acids, particularly natural amino acids, the $CO_2H$ and/or $NH_2$ groups being free or salified, the monomers or mixtures of monomers constituting the chain (P') are the same as those constituting the chain (P) of the products of the formula (I) defined above.

This polymer of formula (II) will advantageously be selected from the following products:

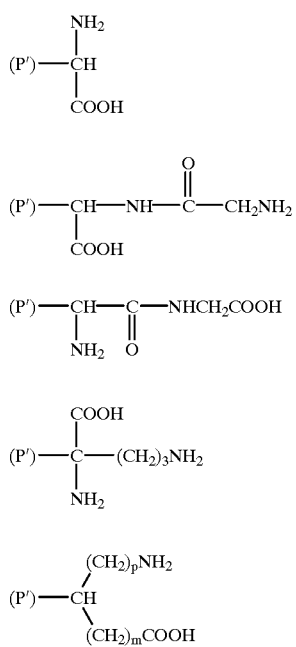

in which (P') is a polymeric chain such as defined above, m and p are integers between 0 and 11 and whose sum is between 2 and 11, or a functionalised polymer obtained by radical polymerisation of at least one monomer in the presence of an amino acid or an amino acid derivative of the formula:

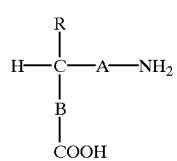

in which R, A and B have the meanings given above.

The products of the formula (II) may be obtained by radical polymerisation of at least one monomer leading to the formation of the hydrophobic polymer chain (P') in the presence of an amino acid or an amino acid derivative of formula (2) below:

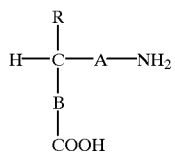

acting as a chain transfer agent during said radical polymerisation.

In the formula (2) above, the R, A and B groups have the meanings given for the same groups in the formula (II).

The role of the chain transfer agent of the product of formula (2) in the radical polymerisation is rendered possible due to the labile character of the hydrogen carried by the carbon in the formula (2) above.

This method, which uses an amino acid or an amino acid derivative as chain transfer agent during the radical polymerisation of at least one monomer leading to the formation of a polymer chain (P'), is inspired by analogy with the method described in the pieces of work by YAMASHITA, CHUJO et al., cited above, in replacing the thiol by an amino acid or an amino acid derivative having a labile hydrogen atom.

More specifically, as it has been pointed out above, the synthesis of PMMAs functionalised with carboxylic acid groups is already known. YAMASHITA, CHUJO et al. have developed this type of macromonomers with the aim of copolymerising them by polycondensation and thus forming grafted copolymers (see in particular E. J. GOETHALS, <Telechelic Polymers Synthesis and Applications> CRC Press, Inc, 169–179 (1989)).

The principle of this synthesis consists of radically polymerising methyl methacrylate in the presence of a transfer agent bearing the acid functions, in this case thiomalic acid, under the conditions indicated in the reaction scheme given above.

The microgels, particularly those obtained from microlatexes prepared from inspiration from various publications cited above of W. FUNKE, are generally introduced in a nail varnish composition after having been swollen in an organic solvent beforehand, the solvent being a solvent of the constituting polymer of the microlatex.

According to a particularly advantageous variant of the invention, one of the constituting solvents of the solvent medium of the nail varnish is used as organic solvent for swelling the microlatex and transforming it into a microgel. This solvent will advantageously be ethyl acetate or butyl acetate.

The constituting particles of the microgel have a diameter between 10 and 300 nm in the swollen state, preferably between 20 and 150 nm, even preferably between 30 and 100 nm.

The microgel in the swollen state will advantageously constituted at least a part of the dry matter comprised in the nail varnish.

Generally, the nail varnishes according to the invention will contain from 1 to 30% by weight of microgels, preferably from 5 to 20%.

The tests carried out by the applicant have shown that the microgels could advantageously replace at least partially the nitrocellulose present in the nail varnish composition, enabling thus obtaining compositions which, for an equal dry extract, have viscosities which are sufficiently low to enable an application of the varnish under good conditions.

Furthermore, other tests carried out by the applicant have shown that the microgels also enabled advantageously replacing at least one part of the organophilic clays present in the nail varnishes, without harming the stability of the dispersion of the pigments within the nail varnish composition. The replacement (at least partial) of the organophilic clays enables the varnish according to the invention to have an improved adhesion on the nail.

Hence, the invention relates particularly to the nail varnishes in which the dry extract is between 20 and 50% by weight, preferably between 25 and 35% by weight.

The invention enables obtaining notably nail varnishes having a high amount of dry extract, for example for preparing nail varnishes of the <one coat> type. It will be possible for the dry extract to reach from 30 to 50% by weight of the varnish.

Furthermore, these nail varnishes contain from 0 to 30% by weight of nitrocellulose, preferably from 0 to 20 %, the nitrocellulose content being as low as the microgel content is high.

On the other hand, the nail varnishes of the invention contain from 0 to 3% by weight of organophilic clay, preferably form 0 to 1.5%, more preferably from 0 to 0.5%. Here again, it is observed that the level of organophilic clay may be as low as the level of microgel is high.

Hence, the use of microgels in the nail varnish compositions of the invention constitute a particularly efficient means of modifying the physical properties of these compositions, as well as those of the film formed during the application of the composition.

More specifically, the use of microgels in the nail varnish compositions enable, in adjusting the dry extract and the viscosity of the composition, regulating at will the rheology of these compositions.

It enables also, as it has been demonstrated by the tests of application of the film formed after applying the nail varnishes, modifying the plasticity of this film in adjusting the content of microgel in the film.

Furthermore, tests also carried out by the applicant have shown that in adjusting the size and the nature of the microgel, as well as the degree of cross-linking, it was possible to modify the brightness of the varnish obtained.

The examples which follow are given as being purely illustrative of the invention.

EXAMPLES

Unless otherwise indicated, the proportions indicated in the Examples below are expressed in percentages by weight.

I-Example of nail varnish composition

A method of the prior art which is well-known to the person skilled in the art is used in all the Examples below of complete compositions of nail varnishes which incorporate microgels. The nail varnishes are prepared from <colouring solutions> of various tints, that is mixed with a nail varnish base.

These <colouring solutions> are in fact dispersions of pigments in a base which contains nitrocellulose, it being possible for this base to be the same as that used for the final formulation of the varnish. Preferably, the pigments are ground beforehand in a solvent, such as butyl acetate by means of an appropriate grinder such as, for example, a ball-grinder of the Dyno-mill type.

The grindings are incorporated into a <diluting> nitrocellulose base in order to prepare various colouring solutions, each one having is own tint according to the nature and the concentration of the pigment that it contains.

For example, the composition of the <diluting> base is the following:

| | | |
|---|---|---|
| nitrocellulose | 10 to 30%, | for example 15% |
| Lustralite ® (arylsulphonamide) | 8 to 15%, | for example 10% |
| dibutyl-phthalate | 4 to 7%, | for example 5% |
| Neocryl ® (acrylic resin) | 0 to 5%, | for example 2% |
| butyl acetate | 5 to 50%, | for example 18% |
| ethyl acetate | 5 to 50%, | for example 17% |
| bentonite | 0.8 to 1.5%, | for example 1% |
| toluene | 0 to 30%, | for example 25% |
| isopropanol | 4 to 13%, | for example 7% |
| | 100% | 100% |

The amount of grinding introduced in the diluting base is such as the pigment concentration in the colouring solution is generally lower than or equal to about 20%.

According to the tint desired of the final composition of the nail varnish, various colouring solutions are introduced in a base, such as the above base, at various concentrations. The pigment content of the final varnish is generally in the order of 2 to 4%.

I.1 Nail varnish which contains a commercial acrylic microgel

A commercial microgel sold by the Nippon Paint Company, and preferably swelled in butyl acetate, is used for the preparation of a nail varnish. This microgel is constituted of particles of 53 nm in diameter. It is constituted based on methyl methylmethacrylate and has a cross-linking level of 0.25 mol/g.

Two nail varnishes designated as a and b are prepared which contain the following proportions:

| | VARNISH a | VARNISH b |
|---|---|---|
| nitrocellulose | 15%, | 10% |
| Lustralite ® (arylsulphonamide) | 10%, | 10% |
| dibutyl-phthalate | 5%, | 5% |
| Neocryl ® (acrylic resin) | 2%, | 2% |
| butyl acetate | 18%, | 18% |
| ethyl acetate | 15%, | 15% |
| bentonite | 0.5%, | 0.5% |
| toluene | 15%, | 15% |
| isopropanol | 6.5%, | 4.5% |
| microgel | 13% | 20% |

I.2 varnish containing microgels obtained form surfactant of the family I a) Microgel a A thiomalic acid-functionalised polymer is prepared which has a PMMA chain of theoretical number average mass of 1,000 in the following way.

The proportions of initiators, transfer agents and monomer have been calculated from the results of YAMASHITA, CHUJO et al. according to the formula:

$$\frac{1}{DPn} = \frac{1}{DPn_0} + Cs\left(\frac{S}{M}\right)$$

In order to prepare a functionalised polymer having a theoretical Mn of 1,000: 1.58 g of AIBN, 33.47 g of thiomalic acid and 100 of MMA are dissolved in 350 ml of THF (tetrahydrofuran).

This solution is placed in a double case reactor equipped with a stirring anchor, a condenser and a nitrogen circulation and is heated at 60° C. for 2 hours and thirty minutes.

The collected mixture is precipitated in petroleum ether once or twice so as to remove the remains of MMA, AIBN and its decomposition products. Dried, it is then dissolved in acetone and reprecipitated several times in water (twice) so as to rid it of the thiol and the disulphide. A determination of the acid functions before and after precipitation demonstrates the efficiency and consequently the necessity of this last purification.

The number molecular mass is:
1,030 (determined by vapour pressure osmometry)
960 (determined by GPC, gel permeation chromatography).

5 of the above polymer are then dissolved in 250 ml of THF.

The number of moles of —COOH functions to be neutralised is determined by an acido-basic determination,: here $7.87 \cdot 10^{-3}$ mol and an excess of base is added i.e. $8.2 \cdot 10^{-3}$ mol.

0.73 g of DMEA (dimethylethanolamine) are dissolved in 500 g of water.

The organic polymer solutions is added slowly with stirring, to the aqueous amine solution.

The mixture obtained is distilled under reduced pressure so as to remove the THF, and is then filtered.

A micellar solution having a Tyndall effect is thus obtained.

The size of the micelles is measured on the Coulter N4 (light diffusion) is about 4.6±1.4 nm.

This type of micelles can be used in the preparation of a microlatex.

An example of formulation of such a latex is given below:
150 g of water,
0.9 of surfactant (neutralised functionalised polymer)
2.7 g of MMA
0.3 g of BDMA (1,4-butanediol dimethylacrylate)
0.075 g of potassium persulphate.
0.046 g of $NaHCO_3$ as buffer.

The polymerisation is carried out in a double case reactor, equipped with a stirring anchor, a condenser and a nitrogen inlet.

The micellar solution is introduced into the reactor where it is heated at 65° C. and deoxygenated for one hour by bubbling in nitrogen. To this solution, stirred at 250 tr/min, is added the mixture of monomers. The initiator is introduced in the form of an aqueous solution after 15 to 20 minutes of emulsification.

The polymerisation is then left to proceed under nitrogen for about 20 hours.

In the case of the preceding formulation, the size of the microlatex obtained is measured on the Coulter N4; the results are the following:
average diameter by weight: Dw=28.6±1.4 nm
average diameter by number: Dn=23.7±3.2 nm The microlatex thus prepared by using the functionalised polymer as surfactant has various advantages summarised below:

The hydrophobic chain is of the same nature as the particle core. There is therefore a contribution in material in addition to the surfactant role.

This microlatex is cross-linked. It may therefore be transferred in solvent medium to give a microgel.

The microlatex cited above was dried and then redispersed in butyl acetate.

The size of the microgel obtained is measured on the Coulter N4: Dw=36.9±0.8 nm.

The swelling of the particles in butyl acetate compared to water is observed.

b) Microgel b

A thiomalic acid functionalised poly(methyl methacrylate-co-allyl methacrylate) is prepared in the following way:

0.32 g of AIBN, 0.69 g of thiomalic acid, 4 g of allyl methacrylate and 16 g of MMA are dissolved in 70 ml of THF.

This solution is placed in a double cased reactor equipped with a stirring anchor, a condenser and a nitrogen circulation, and is heated at 60° C. for 2 hours and thirty minutes.

The mixture collected is precipitated in petroleum ether. Dried, it is then dissolved in acetone and reprecipitated in water (twice).

The number molecular mass is:
1,420 (determined by GPC)
1,500 (determined by VPO, vapour pressure osmometry).

Then, 2.5 g of this polymer are dissolved in 250 ml of THF.

According to the acido-basic determination in THF medium of the polymer with potassium hydroxide, there are $2.98 \cdot 10^{-3}$ moles of —COOH to neutralise. An excess of base is used, here $3.37 \cdot 10^{-3}$ moles, for neutralising, making 0.3 g of DMEA.

These 0.3 g of DMEA are dissolved in 250 ml of water.

The organic polymer solution is added slowly with stirring to the aqueous amine solution. The mixture obtained is distilled under reduced pressure so as to remove the THF, and is then filtered.

The size of the micelles measured on the Coulter N4 is about 5.5±0.6 nm.

This type of micelles may be used in the preparation of microlatex.

A microlatex is prepared as in Example 2 and under the same conditions.

The size of the microlatex thus obtained is measured on the Coulter N4:
Dw=27.4±1.6 nm
Dn=22.5±2.5 nm.

The same advantages as in the preceding Example are obtained with this functionalised polymer:
contribution of material as in the preceding Example
the hydrophobic chain of the polymer consists of pendant allylic groups which are capable of copolymerising with the particle core.

The surfactant is then chemically linked to the particle.

The cross-linked microlatex cited above was dried and then redispersed in butyl acetate.

The size of the microgel (b) obtained is measured on the Coulter N4:
Dw=38.8±2.0 nm.

c) Microgel c

A polymer constituted by PPMA of Mn equal to 3,380 is prepared which is chain end-functionalised with cysteine.

Carried out as in Examples a and b above under the following operating conditions:
40 g of MMA
8.76 g of cysteine
0.63 g of AIBN
320 g of acetic acid
80 g of water
T=60° C.
Duration of polymerisation: 5 hours.

Then, the 2.5 g of the above polymer are dissolved in 250 ml of THF.

The number of moles of —COOH functions to be neutralised is determined by an acido-basic determination in THF medium: here 7.4 $10^{-4}$ moles and an excess of base, making about 8.5 $10^{-4}$ moles, is added.

8.5 $10^{-4}$ moles of potassium hydroxide are diluted in 250 ml of water.

The organic polymer solution is added slowly, with stirring, to the aqueous solution of potassium hydroxide.

The mixture obtained is distilled under reduced pressure so as to remove the THF, and then filtered on Goosh of No. 4 porosity.

The resulting solution may be used in the preparation of microlatex.

A microlatex of the following formulation is prepared:

150 g of water 0.35 g of surfactant (neutralised functionalised polymer)

2.7 g of MMA 0.3 g of BDMA

2×0.075 g of AIBN 0.046 g of NaHCO$_3$

The polymerisation is carried out in a double cased reactor, equipped with a stirring anchor, a condenser and a nitrogen inlet.

The emulsion constituted of water, the surfactant, monomers and NaHCO$_3$ is prepared under strong stirring and is deoxygenated by bubbling in nitrogen.

0.075 g of AIBN dissolved in 2 g of acetone are introduced after 15 to 20 minutes.

After 4 hours, 0.075 of AIBN in 2 g of acetone are re-introduced in the reactor.

The polymerisation is then left to proceed under nitrogen for about 20 hours.

In the case of the preceding formulation, the size of the latex obtained is measured on the Coulter N4. The results are the following:

average diameter by weight: Dw=63.0±1.7 nm average diameter by number: Dn=59.7±2.5nm The microlatex thus prepared by using the functionalised polymer as surfactant has various advantages summarised below:

the hydrophobic chain is of the same nature as the core of the particle. There is therefore a contribution of material in addition the surfactant role.

This microlatex is cross-linked. It may therefore be transferred in a solvent medium to give a microgel.

This microlatex is transferred in butyl acetate. Microgel (c) is obtained.

d) Three nail varnishes are prepared by introducing 5% by weight of each one of the microgels a, b and c described above into the base cited above.

II-Demonstration of the influence of the microgels on the physical properties of the nail varnishes II.1. Influence on the rheology:

The compositions represented in the Table I below, given with their flow thresholds are carried out with the aid of commercial microgel used in Example I.1.

TABLE I

| Microgel | Nitrocellulose | Solvent | Flow threshold dyne/cm |
|---|---|---|---|
| 0.93 | 17.6 | 81.5 | 0.17 |
| 7.8 | 14 | 78.3 | 0.23 |

TABLE I-continued

| Microgel | Nitrocellulose | Solvent | Flow threshold dyne/cm |
|---|---|---|---|
| 10.8 | 13 | 76.3 | 2.85 |
| 15.4 | 10.8 | 73.8 | 3.24 |
| 20 | 9 | 71 | 94.7 |
| 26.9 | 5.9 | 67.2 | 755 |

It arises that in order to obtain satisfactory results from the point of view of rheological behaviour, it is necessary to incorporate microgel concentrations of 15 to 20%. The product obtained is viscous and fluid when the brush is used.

Insofar as it appears that the viscosity increases relatively little with the microgels in low concentration, the use of microgels enable increasing the dry extract without varying the viscosity too much.

TABLE II

| Composition | Viscosity in mPa · s |
|---|---|
| 20% Nitrocellulose E35 | 600 |
| 15% Nitrocellulose E35 | 200 |
| 5% Microgel | |
| 15% Nitrocellulose E35 | 150 |

II. Influence of the microgel on the plasticity of the nitrocellulose films comparative tests of film rupture after application are carried out.

For this, three nail varnish compositions (designated a, b and c) are prepared:

composition a is carried out by using a diluting base such as defined in Example I, but without dibutyl phthalate;

composition b is carried out with the same base, but which contains an mount of dibutyl phthalate which represents 25% of the dry extract;

composition c is obtained by replacing in composition b, the dibutyl phthalate by the same quantity of the commercial microgel used in Example I.1.

The tests of application upon rupture of the film show that the microgel confers to the film the same plasticity as the dibutyl phthalate (the values of application upon rupture differ by less than 5%).

What is claimed is:

1. Nail varnish comprising:

an organic solvent having at most 1% water;

at least one microgel, said microgel being a three-dimensional, cross-linked polymer having a diameter less than about 100 nm when in particulate form in a non-swollen state, said microgel resulting from polymerization in an emulsion or dispersion of a monofunctional main monomer and a difunctional monomer acting as a cross-linking agent, said main monomer being an acrylic monomer, methacrylic monomer, styrenic monomer, or vinylic ester monomer having a C1 to C18 alkyl group, and said difunctional monomer being a diacrylic or dimethacrylic monomer, or a difunctional aromatic monomer, and not being obtained from an acrylic polymer microdispersion prepared by a radical polymerisation of at least one acrylic monomer in the presence of a poly(methylmethacrylate) (PMMA)- and poly(tertbutylacrylate) (PtBuA)-based block copolymer; and an effective amount of a nail varnish pigment.

2. Nail varnish according to claim 1 wherein said microgel is obtained by swelling, in a solvent of the crosslinked polymer, a microlatex prepared by radical polymerisation of said main monomer in the presence of said difunctional monomer and a surfactant.

3. Nail varnish according to claim 2, wherein the surfactant is a macromolecular surfactant.

4. Nail varnish according to claim 2, wherein said surfactant is a polyester functionalised with carboxylic groups.

5. Nail varnish according to claim 2, wherein said surfactant is a functionalised polymer of the formula:

(P)—S—X—F  (1)

in which:
- (P) is a hydrophobic polymer chain of number average molar mass between 500 and 250,000,
- S represents sulphur,
- X represents:
  - a saturated or unsaturated linear or branched hydrocarbon chain having 1 to 6 carbon atoms and substituted with at least on COOH or NH$_2$ group, in the free or salified form;
  - a peptide chain constituted of 2 to 4 amino acids,
- F represents a COOH or NH$_2$ group, in the free or salified form, or a polymer resulting from the radical polymerisation of at least one monomer in the presence of a peptide bearing at least one disulphide group and/or at least one thiol function.

6. Nail varnish according to claim 5, wherein said functionalised polymer results from the radical polymerisation of a monomer in the presence of a thiol of the formula H—S—X—F or a disulphide of formula F—X—S—S—X—F in which:
- X represents:
  - a saturated or unsaturated linear or branched hydrocarbon chain having 1 to 6 carbon atoms and substituted with at least one COOH or NH$_2$ group, in the free or salified form,
  - a peptide chain constituted of 2 to 4 amino acids,
- F represents a COOH or NH$_2$ group, in the free or salified form, said thiol or disulphide acting as chain transfer agent during said radical polymerisation, said monomer (s) leading to the formation of the polymer chain (P).

7. Nail varnish according to claim 5 wherein the polymer chain (P) has a number average molar mass lower than 20,000.

8. Nail varnish according to claim 5 wherein X—F comprises at least one carboxylic function and at least one amine function, in the free or salified form.

9. Nail varnish according to claim 5 wherein said functionalised polymer is of formula:

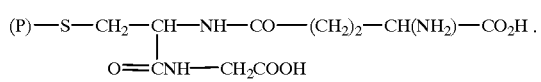

10. Nail varnish according to claim 9, wherein said functionalised polymer is obtained by radical polymerisation of a monomer leading to the polymerised chain in the presence of a chain transfer agent constituted by glutathione.

11. Nail varnish according to claim 5 wherein said functionalised polymer is obtained by radical polymerisation of at least one monomer in the presence of cysteine or homocysteine acting as chain transfer agent.

12. Nail varnish according to claim 5 wherein said functionalised polymer is obtained by radical polymerisation of at least one monomer in the presence of a peptide bearing at least one disulphide group and/or at least one thiol function.

13. Nail varnish according to claim 5 wherein said polymer chain (P) results from the radical polymerisation of at least one acrylic or vinylic monomer.

14. Nail varnish according to claim 2 wherein said surfactant is a chain end-functionalised polymer of the formula:

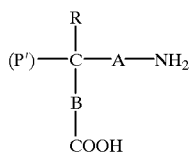

in which:
- the polymer chain (P') is hydrophobic chain obtained by radical polymerisation of at least one monomer, and whose number average molar mass is between 500 and 250,000,
- R represents a hydrogen atom or a linear or branched hydrocarbon chain having 1 to 8 carbon atoms optionally substituted with at least one group selected from CO$_2$H, NH$_2$, OH or phenyl group, itself being optionally substituted,
- A and B, identical or different, each represent a single bond, a saturated or unsaturated linear or branched hydrocarbon chain having from 1 to 16 carbon atoms, it being possible for it to contain an amide bond or a peptide chain having 2 to 4 amino acids,
- the CO$_2$H and/or NH$_2$ groups being free or salified.

15. Nail varnish according to claim 14, wherein said functionalised polymer is of one of the following formulae:

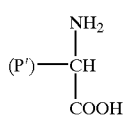

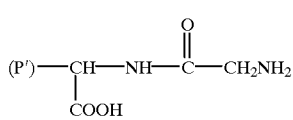

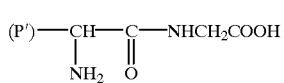

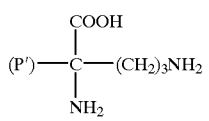

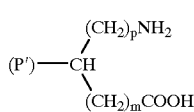

m and p are integers between 0 and 11 and whose sum is between 2 and 11, or a functionalised polymer obtained by radical polymerisation of at least one monomer in the presence of an amino acid or an amino acid derivative of the formula:

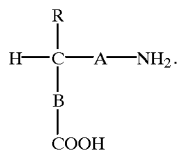

(2)

16. Nail varnish according to claim 1 wherein said microgel is constituted of microparticles which in the swollen state have a diameter between 10 and 300 nm.

17. Nail varnish according to claim 1 wherein said microgel is present in said nail varnish in an amount from 1 to 30% by weight.

18. Nail varnish according to claim 17, wherein the dry extract represents from 20 to 50% by weight.

19. Nail varnish according to claim 1 further comprising from 0 to 30% by weight of nitrocellulose.

20. Nail varnish according to claim 1 further comprising from 0 to 3% by weight of organophilic clay.

21. Nail varnish according to claim 1 wherein said microgel is present in an effective amount to increase the amount of dry extract in said varnish without substantially increasing its viscosity.

22. Nail varnish according to claim 1 wherein said nail varnish pigment is present in an amount of 2 to 4%.

23. Nail varnish according to claim 1 wherein said main monomer is selected from the group consisting of:
   alkylacrylates having linear or branched C1 to C6 groups, alkylmethacrylates having linear or branched C1 to C6 groups, or a mixture thereof, and
   vinyl ester having a C1 to C8 alkyl groups; and said difunctional monomer being selected from the group consisting of:
      butandiol dimethacrylate, ethyleneglycol dimethacrylate, diethyleneneglycol dimethacrylate, tetraethyleneglycol dimethacrylate and divinyl benzene.

24. Nail varnish according to claim 1 wherein said main monomer is selected from the group consisting of:
   methacrylates with C1 to C18 groups, styrene, alpha-methyl styrene, acrylonitrile, vinyl acetate, or mixtures thereof.

25. Nail varnish according to claim 1 wherein said main monomer is methyl methacrylate and the difunctional monomer is butandiol dimethylacrylate.

26. The nail varnish of claim 1 wherein said microgel is polymerized in an emulsion in water.

27. A method for modifying the physical properties of a nail varnish composition comprising an organic solvent having at most 1% water and an effective amount of a nail varnish pigment by incorporating at least one microgel in said nail varnish composition, said microgel being a three-dimensional, cross-linked polymer having a diameter less than about 100 nm when in particulate form in a non-swollen state, said microgel resulting from polymerization in an emulsion or dispersion of a monofunctional main monomer and a difunctional monomer acting as a cross-linking agent, said main monomer being an acrylic monomer, methacrylic monomer, styrenic monomer, or vinylic ester monomer having a C1 to C18 alkyl group, and said difunctional monomer being a diacrylic or dimethacrylic monomer, or a difunctional aromatic monomer, and not being obtained from an acrylic polymer microdispersion prepared by a radical polymerisation of at least one acrylic monomer in the presence of a poly(methylmethacrylate (PMMA)- and poly (tert-butyl acrylate) (PtBuA)-based block copolymer.

28. Nail varnish according to claim 27, wherein said microgel improves the plasticity of a film formed by said nail varnish after said nail varnish has been applied to a fingernail and dried to form said film on said fingernail.

29. The method of claim 27, wherein said microgel regulates the rheology of said nail varnish composition.

30. The method according to claim 27 wherein said nail varnish pigment is present in an amount of 2 to 4%.

31. The method according to claim 27 wherein said main monomer is selected from the group consisting of:
   alkylacrylates having linear or branched C1 to C6 groups, alkylmethacrylates having linear or branched C1 to C6 groups, or a mixture thereof, and
   vinyl ester having a C1 to C8 alkyl groups; and said difunctional monomer being selected from the group consisting of:
      butandiol dimethacrylate, ethyleneglycol dimethacrylate, diethyleneneglycol dimethacrylate, tetraethyleneglycol dimethacrylate and divinyl benzene.

32. Nail varnish according to claim 27 wherein said main monomer is selected from the group consisting of:
   methacrylates with C1 to C18 groups, styrene, alpha-methyl styrene, acrylonitrile, vinyl acetate, or mixtures thereof.

33. Nail varnish according to claim 27 wherein said main monomer is methyl methacrylate and the difunctional monomer is butandiol dimethylacrylate.

34. Nail varnish comprising an organic solvent having at most 1% water, at least one microgel, said microgel being a three-dimensional, cross-linked polymer having a diameter less than about 100 nm when in particulate form in a non-swollen state, said microgel resulting from polymerization in an emulsion or dispersion of a monofunctional main monomer and a difunctional monomer acting as a cross-linking agent, said main monomer being an acrylic monomer, methacrylic monomer, styrenic monomer, or vinylic ester monomer having a C1 to C18 alkyl group, and said difunctional monomer being a diacrylic or dimethacrylic monomer, or difunctional aromatic monomer, and not being obtained form an acrylic polymer microdispersion prepared by a radial polymerisation of at least one acrylic monomer in the presence of a poly(methylmethacrylate) (PMMA)- and poly(tert-butylacrylate) (PtBuA)-based block copolymer and an effective amount of a nail varnish pigment, said microgel being present in an effective amount to obtain a nail varnish having a dry extract comprised between 20 and 50% by weight of said varnish.

35. Nail varnish according to claim 34 wherein said dry extract comprises between 25 and 35% by weight of said varnish.

36. Nail varnish according to claim 34 wherein said nail varnish pigment is present in an amount of 2 to 4%.

37. Nail varnish according to claim 34 wherein said main monomer is selected from the group consisting of:
   alkylacrylates having linear or branched C1 to C6 groups, alkylmethacrylates having linear or branched C1 to C6 groups, or a mixture thereof, and
   vinyl ester having a C1 to C8 alkyl groups; and said difunctional monomer being selected from the group consisting of:

butandiol dimethacrylate, ethyleneglycol dimethacrylate, diethyleneneglycol dimethacrylate, tetraethyleneglycol dimethacrylate and divinyl benzene.

38. Nail varnish according to claim 34 wherein said main monomer is selected from the group consisting of:
methacrylates with C1 to C18 groups, styrene, alpha-methyl styrene, acrylonitrile, vinyl acetate, or mixtures thereof.

39. Nail varnish according to claim 34 wherein said main monomer is methyl methacrylate and the difunctional monomer is butandiol dimethylacrylate.

40. A one-coat nail varnish comprising an organic solvent having at most 1% water, at least one microgel, said microgel being a three-dimensional, cross-linked polymer having a diameter less than about 100 nm when in particulate form in a non-swollen state, said microgel resulting from polymerization in an emulsion or dispersion of a monofunctional main monomer and a difunctional monomer acting as a cross-linking agent, said main monomer being an acrylic monomer, methacrylic monomer, styrenic monomer, or vinylic ester monomer having a C1 to C18 alkyl group, and said difunctional monomer being a diacrylic or dimethacrylic monomer, or a difunctional aromatic monomer, and not being obtained from an acrylic polymer microdispersion prepared by a radical polymerisation of at least one acrylic monomer in the presence of a poly(methylmethacrylate) (PMMA)- and poly(tertbutylacrylate (PtBuA)-based block copolymer and an effective amount of a nail varnish pigment, said microgel being present in an effective amount to obtain a nail varnish having a dry extract comprised between 30 and 50% by weight of said varnish.

41. Nail varnish according to claim 40 wherein said nail varnish pigment is present in an amount of 2 to 4%.

42. Nail varnish according to claim 40 wherein said main monomer is selected from the group consisting of:
alkylacrylates having linear or branched C1 to C6 groups, alkylmethacrylates having linear or branched C1 to C6 groups, or a mixture thereof, and
vinyl ester having a C1 to C8 alkyl groups; and said difunctional monomer being selected from the group consisting of:
butandiol dimethacrylate, ethyleneglycol dimethacrylate, diethyleneneglycol dimethacrylate, tetraethyleneglycol dimethacrylate and divinyl benzene.

43. Nail varnish according to claim 40 wherein said main monomer is selected from the group consisting of:
methacrylates with C1 to C18 groups, styrene, alpha-methyl styrene, acrylonitrile, vinyl acetate, or mixtures thereof.

44. Nail varnish according to claim 40 wherein said main monomer is methyl methacrylate and the difunctional monomer is butandiol dimethylacrylate.

* * * * *